United States Patent [19]

Seko et al.

[11] Patent Number: 4,602,247
[45] Date of Patent: Jul. 22, 1986

[54] METHOD AND SYSTEM FOR DETECTING DRIVER FATIGUE INCLUDING DIFFERENTIATION OF EFFECTS OF REST PERIODS

[75] Inventors: Yasutoshi Seko, Yokohama; Haruhiko Iizuka, Yokosuka; Takayuki Yanagishima, Yokosuka; Hideo Obara, Yokosuka, all of Japan

[73] Assignee: Nissan Motor Company, Limited, Japan

[21] Appl. No.: 580,176

[22] Filed: Feb. 15, 1984

[30] Foreign Application Priority Data

Feb. 18, 1983 [JP] Japan .............................. 58-22818[U]
Feb. 18, 1983 [JP] Japan .............................. 58-22819[U]

[51] Int. Cl.⁴ ............................................. G08B 23/00
[52] U.S. Cl. .................................... 340/575; 180/272
[58] Field of Search .................... 340/575, 576, 52 D, 340/52 R; 180/272

[56] References Cited

U.S. PATENT DOCUMENTS 4,348,663 9/1982 Yanagishima et al. ............. 340/576
4,502,122 2/1985 Yanagishima .................... 340/575 X

FOREIGN PATENT DOCUMENTS 48492 9/1981 European Pat. Off. .

Primary Examiner—James L. Rowland
Assistant Examiner—Jeffery A. Hofsass
Attorney, Agent, or Firm—Lowe, Price, LeBlanc, Becker & Shur

[57] ABSTRACT

A fatigue alarm system and method for an automotive vehicle driver is adapted to measure periods of time during which the vehicle is driven and to subtract therefrom periods of time during which the driver rests. The driver rest periods are distinguished from brief stops of the vehicle in order to accurately measure the adjusted period of driving time. In order to distinguish rest periods from brief traffic stops, the duration of vehicle stops are measured and compared with a given value. When the vehicle stop periods are shorter than the given value, the vehicle is judged to be stopped briefly, i.e. that the driver is not resting, and the measured driving period is incremented by the measured vehicle stop period. On the other hand, when the stop periods are longer than the given value, the driver is judged to be resting. In this case, the measured stop time is subtracted from the measured driving time after being adjusted by a suitable proportionality factor. The result of measurement is visually displayed by means of a plurality of fatigue level indicator segments. The threshold levels at which each indicator segment is activated or deactivated in adjusted in accordance with its current activation state in order to avoid hunting thereof.

14 Claims, 5 Drawing Figures

METHOD AND SYSTEM FOR DETECTING DRIVER FATIGUE INCLUDING DIFFERENTIATION OF EFFECTS OF REST PERIODS

BACKGROUND OF THE INVENTION

The present invention relates generally to a fatigue alarm system and method for an automotive vehicle driver for detecting fatigue accumulated during vehicle driving and cautioning the driver when the driver's accumulated fatigue reaches a predetermined level. More particularly, the invention relates to a fatigue alarm system for detecting accumulated driver fatigue by measuring the period of time for which the driver has been driving.

It is well known that it is recommendable to take a rest after every two or two and a half hours of driving in order to refresh oneself and recover from driving fatigue. It is especially necessary for the driver to take a rest after driving for a relatively long time.

Various alarm devices for producing rest suggestions have been developed and proposed. For example, published Japanese Utility Model (Jikko Sho) No. 48-15104 shows an alarm device which is associated with a tachograph to produce an alarm at a given time. On the other hand, unexamined Japanese Utility Model (Jikkai Sho) No. 51-156878 shows a device for displaying a required resting period of time depending on the preceding driving period.

Since the foregoing devices are adapted to deliver messages to the driver at certain fixed times, the alarm timing does not always correspond to the driver's fatigue. For example, if the driver takes a rest before the given time or if driving conditions vary significantly, the fixed alarm timing will not correspond to the driver's fatigue.

To ameliorate the above-mentioned defect, Published Japanese Utility Model (Jikkai Sho) No. 52-13232 shows another alarm device which counts the pulses of a clock signal in order to detect the timing at which to give the alarm. In this device, the timing is detected by analog processing of the clock signal.

In addition, Published Japanese Utility Model (Jikkai Sho) No. 51-156878 discloses an alarm device adapted to detect accumulation of fatigue of an automotive vehicle driver and to set an alarm clock to produce an alarm. The detection of accumulation of fatigue is based on selected driving conditions of the vehicle and the period of time for which the detected driving conditions are maintained. Fatigue data obtained on the basis of the driving conditions and the time is integrated to derive a correction or update value for the preset time, which is to be compared with the actual driving time. The alarm device is activated when the driving time reaches the updated time.

In this case, in order to measure the total driver fatigue accurately, it is necessary to reduce the fatigue total value in accordance with the rests taken by the driver in order to reflect the practical fatigue condition of the driver. On the other hand, even when the vehicle is at rest and preselected rest parameters, such as a vehicle speed of zero and application of a parking brake, are satisfied, the driver is not necessarily resting. Vehicle conditions similar to those extant during driver rest-periods may occur even while driving. For example, when the vehicle comes to rest at a stop signal, the driver is apt to apply the parking brake. If application of the parking brake and zero vehicle speed are taken as parameters indicating that the driver is resting, then such cases as described above may also be regarded as resting time.

This would degrade the accuracy of detection of the driver fatigue. Therefore, in order to monitor the driver's fatigue accurately, it is necessary to distinguish whether or not vehicle rest corresponds to the driver's rest.

SUMMARY OF THE INVENTION

Therefore, it is an object of the present invention to provide a fatigue alarm system and method for an automotive vehicle driver, which is capable of distinguishing between periods of driver rest and brief stops of the vehicle so that accumulated driver fatigue may be accurately monitored.

Another object of the invention is to provide a fatigue alarm system and method including a display showing accumulated fatigue to inform the driver thereof. The display is so designed that even when driving conditions vary radically, hunting, i.e. excessively frequent ON and OFF switching by the display, is avoided.

In order to accomplish the above-mentioned and other objects, a fatigue alarm system for an automotive driver has means responsive to the vehicle being at rest for measuring the period of time for which the vehicle remains at rest. The measured period of time is compared with a predetermined threshold in order to distinguish between a driver rest stop and a brief stop due to traffic, road or vehicle conditions. If the measured period of time is longer than the threshold, the driver is judged to be resting and thus the measured period of time is subtracted from an accumulated driving time which is continuously updated while the vehicle is moving. On the other hand, if the measured period of time is shorter than the threshold, the measured period of time is regarded as part of driving time and thus is added to the accumulated driving time. Based on the measured accumulated driving time, the fatigue condition of the driver is judged and an alarm is generated when driver fatigue is judged to exceed a predetermined level.

Preferably, the alarm is given to the driver in the form of visual display which has a plurality of indicator segments, each of which is adapted to be turned ON when the measured driving time exceeds a corresponding threshold level. The threshold levels to be compared with the measured driving time to determine the activation state of the various indicator segment are adjusted depending upon the indicator segment activation conditions. When an indicator segment is turned ON, the corresponding threshold level is lowered at a given rate or value so that hunting by the indicator segment will not occur.

In accordance with one aspect of the invention, a fatigue alarm system for an automotive vehicle driver comprises, a first means for measuring a period of time in which an ignition switch is maintained at ON position to derive a first signal having a value representative of the measured driving period of time, a second means for measuring a period of time in which the ignition switch is maintained at OFF position to derive a second signal having a value representative of the measured resting time, a detector for detecting a vehicle stopping condition while the ignition switch is maintained at ON position to produce a detector signal, a third means, responsive to the detector signal, for measuring a period of time in which the detector signal is maintained to derive a third signal having a value representative of the measured stopping time, a fourth means for subtracting the second signal value from the first signal value to derive an accumulated driving time data, the fourth means comparing the third signal value with a first threshold so that, when the third signal value is less than the first threshold, the third signal value is added to the accumulated driving time data, and when the third signal value is larger than the first threshold, the third signal value is subtracted from the driving time data, and the fourth means further comparing the driving time data with a second threshold to produce an alarm signal when the value of the driving time data is larger than the second threshold, and an alarm means, responsive to the alarm signal from the fourth means for producing an alarm.

Preferably, the alarm means comprises a visual display including a plurality of indicator segments and an alarming segment turned ON in response to the alarm signal, said indicator segments being adapted to indicate accumulated condition of drivers fatigue, each of the fatigue accumulation indicative segments being responsive to the driving time data value exceeding a corresponding given level which corresponds fatigue level to be indicated.

BRIEF DESCRIPTION OF THE DRAWINGS

The present invention will be understood more fully from the detailed description given herebelow and from the accompanying drawings of the preferred embodiment of the invention, which, however, should not be taken to limit the invention to the specific embodiment but are for explanation and understanding only.

In the drawings.

DESCRIPTION OF THE PREFERRED EMBODIMENTS

Figure 1:
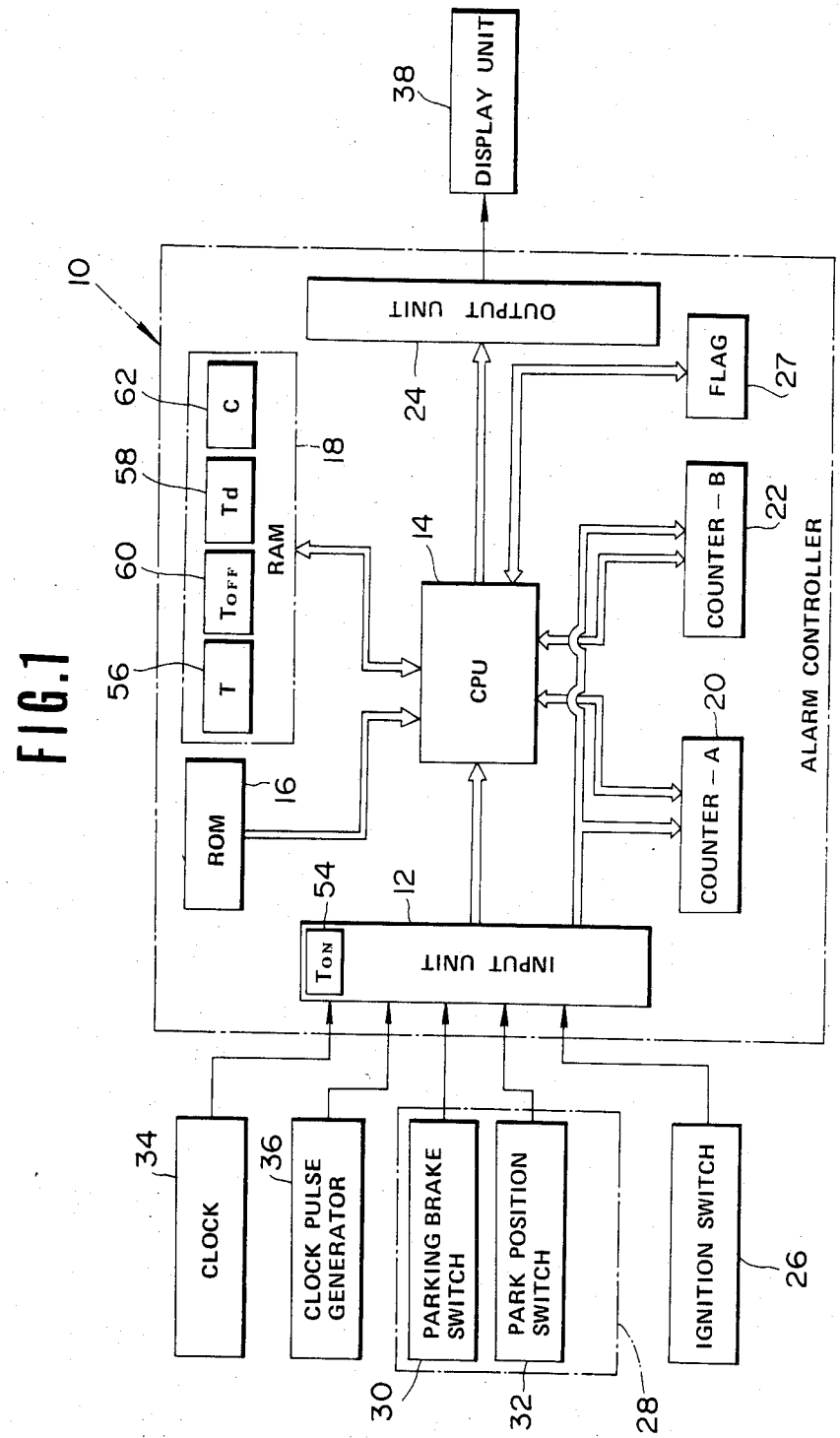
FIG. 1 is a schematic block diagram of the preferred embodiment of a fatigue alarm system according to the present invention.

Referring now to the drawings, particularly to FIG. 1, the preferred embodiment of a fatigue alarm system according to the present invention employs an alarm controller 10 comprising a microcomputer. The controller 10 has an input unit 12, CPU 14, ROM 16, RAM 18, counter-A 20, counter-B 22 and an output unit 24. An ignition switch 26 is connected to the controller 10 via the input unit 12 and delivers an ignition ON signal $S_1$ as long as it remains in its ON position. A vehicle stop detector 28 is also connected to the controller 10 via the input unit 12. The vehicle stop detector 28 is adapted to detect when vehicle is at rest by detecting one or more vehicle stop parameters such as the applied position of a parking brake, the park gear position of an automatic transmission, and/or a vehicle speed sensor signal indicative of zero vehicle speed.

In the shown embodiment, a parking brake switch 30 and an automatic transmission park position switch 32 are used to detect when the vehicle is at rest. The parking brake switch 30 outputs a park position indicative signal $S_2$ as long as the automatic transmission remains in its park position. Although the parking brake switch and the automatic transmission park position switch are used in the illustrated embodiment, the vehicle stop detector 28 can comprise any other appropriate detectors or sensors which can detect that vehicle has stopped. Further, in the shown embodiment, the automatic transmission park position switch is not always required and can be omitted, especially in cases of vehicles with manual transmission.

The controller 10 is also connected to a vehicle clock 34 supply real-time data continuously. The real-time data output from the vehicle clock 34 consists, in practice, of a month element, a date element, an hour element and a clock pulse generator 36 continuously outputting clock pulses. The clock pulses from the clock pulse generator 36 are supplied to the counter-A 20 and the counter-B 22 selectively to be counted. The counter-A 20 is adapted to measure a period of time $t_A$ while the vehicle is running. On the other hand, the counter-B 22 is adapted to measure a period of time $t_B$ while the vehicle is at rest. The counter-A and the counter-B respectively supply time data $t_A$ and $t_B$ to the CPU when accessed. In addition, the counter-A and the counter-B are adapted to be cleared when the counter values thereof are read out or upon being disabled.

The controller 10 is connected for output to a display unit 38 which is adapted to display fatigue data as an alarm or caution. The display unit 38 in the shown embodiment displays fatigue data via a visual display indicator, which fatigue data is derived from an accumulated driving time value $T_d$. Although the shown embodiment uses a visual display to deliver the alarm to the fatigued driver, it is also possible to replace it with another alarm device, such as an audible warning device.

Figure 2:
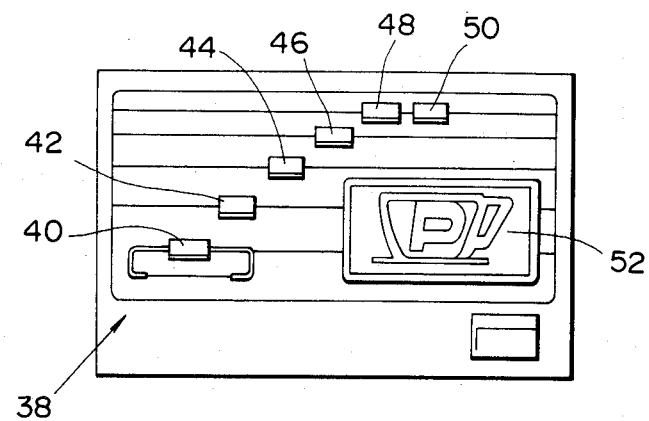
FIG. 2 is a front elevation of a display unit employed in the preferred embodiment of alarm system of FIG. 1.

As shown in FIG. 2, the display unit 38 includes a plurality of indicator segments 40, 42, 44, 46, 48, 50 and 52. The indicator segment 40 is turned ON in response to system activation and remains ON as long as the system is in operation. This indicator segment 40 will be referred to hereafter as "operation monitor". The segments 42, 44, 46, 48 and 50 are adapted to indicate the level of accumulated fatigue of the vehicle driver based on the assumption that fatigue accords with accumulated time after starting the engine.

Figure 3:
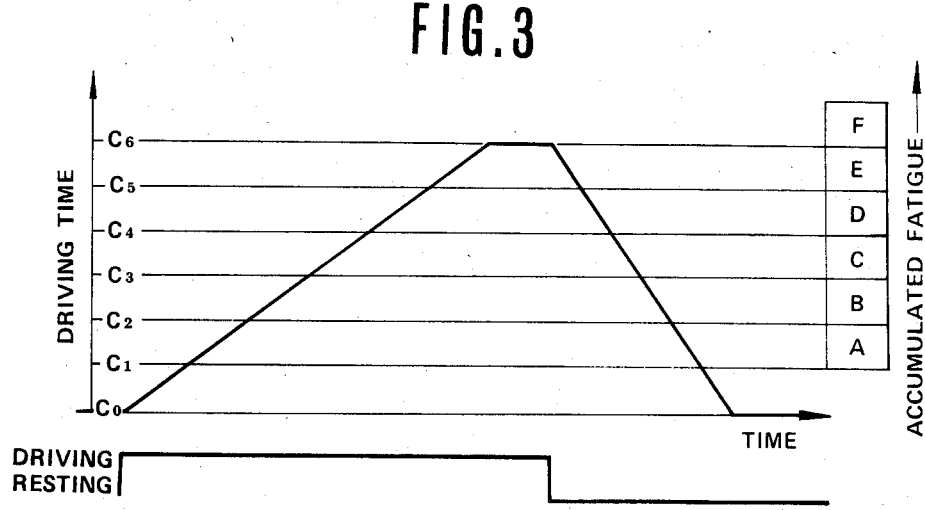
FIG. 3 shows an example of the relationship between driving/resting periods and accumulated fatigue during driving.

In practical operation, the indicator segments 42, 44, 46, 48 and 50 light up in sequence, one for every 30 minutes of driving time. For instance, when accumulated driving time after engine start-up exceeds a first indicator ON threshold $C_1$, which corresponds to the level A in FIG. 3, the first indicator segment 42 is turned ON. After the vehicle has travelled an additional thirty minutes, i.e. when driving time reaches one hour, so that the time value exceeds the second indicator ON threshold $C_2$, which corresponds to the level B in FIG. 3, the second indicator 44 is turned ON. Similarly, when driving time exceeds 1.5 hours so that the time data exceeds the third indicator ON threshold $C_3$, corresponding to level C of FIG. 3, the third indicator 46 is turned ON, and so on.

After the fifth indicator 50 is turned ON, if the driver continues to drive, then the alarm indicator 52 is turned ON to inform the driver that it is time to take a rest since accumulated fatigue is beyond the level at which the driver can drive safely. As will be appreciated from FIG. 2, the alarm indicator 52 covers a relatively large display area in order to attract the driver's attention. It would also be effective to use different colors for each of the first to fifth indicators and the alarm indicator to further attract the driver's attention.

On the other hand, when the vehicle is stopped and the stopping of the vehicle is detected by means of the parking brake switch 30 and/or automatic transmission park position switch 32, the period of time for which the vehicle remains at rest is decremented from the accumulated time value. If the period to be subtracted from the total is long enough to reduce the time value to below the fifth indicator OFF threshold, which is the same as the fourth indicator ON threshold, the fifth indicator 50 is turned OFF. Likewise, when the time value is reduced less than the fourth indicator OFF threshold, which is the same as the third indicator ON threshold, the fourth indicator 48 is turned OFF, and so on until the accumulated time value is decremented to zero (Co in FIG. 3), at which time the first indicator 42 is turned off.

Since the time required to recover from fatigue, i.e. to refresh the vehicle driver, will generally be shorter than that needed to accumulate the corresponding fatigue, the decrement rate of the time value corresponding to the period of time during which the vehicle is at rest should be greater than the rate of increase while driving. In practice, this decrement rate should be about four times as great as the time increment rate. Therefore, the accumulated time value is obtained from the following formula:

$$T = T_d - 4 \times T_r,$$

where

T is the accumulated time value, $T_d$ is the total period of driving time of the vehicle; and $T_r$ is total period of rest time of the vehicle.

Figure 4:
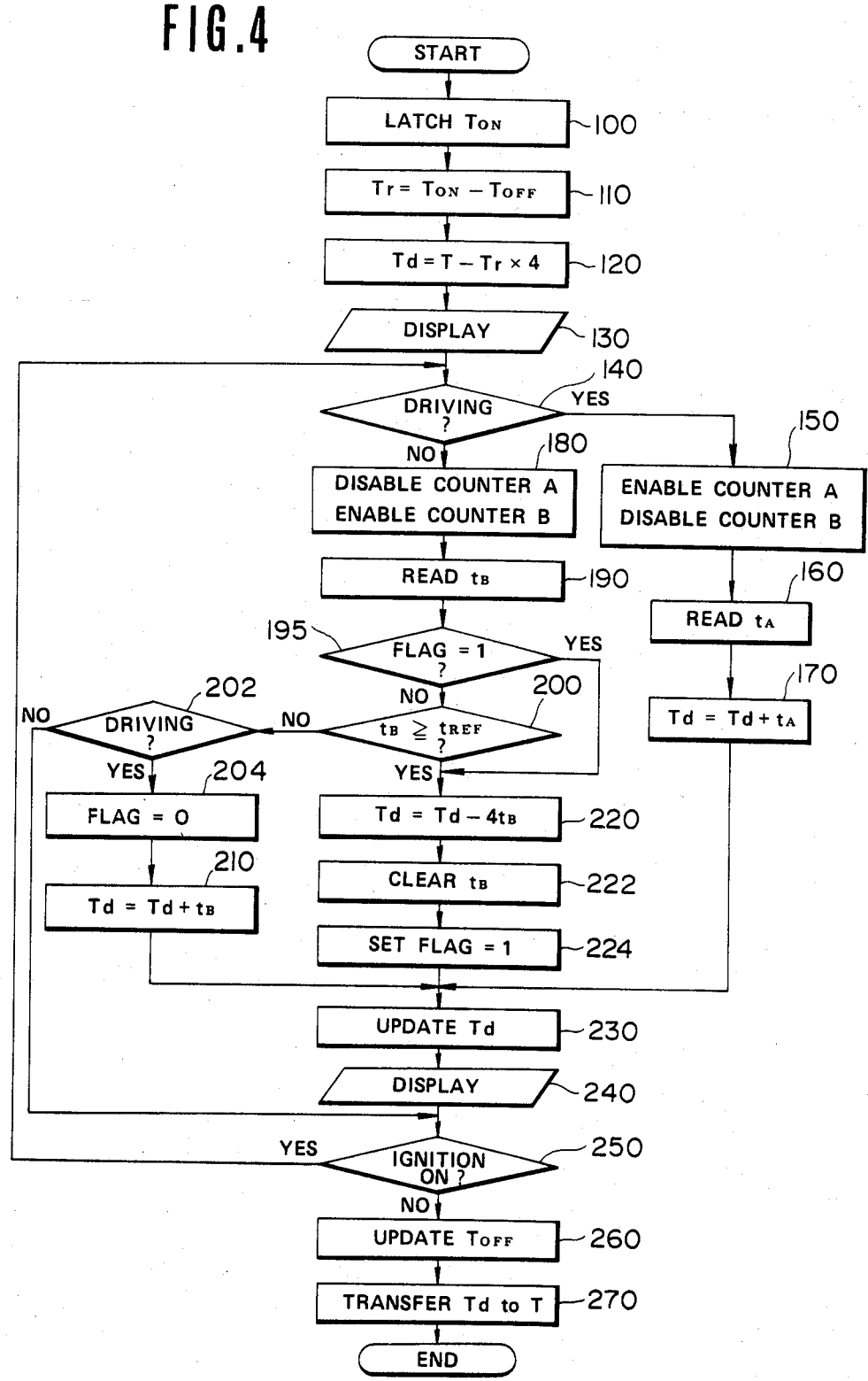
FIG. 4 is a flowchart of a main routine performing the alarm operation in the fatigue alarm system of FIG. 1.

FIG. 4 is a microcomputer flowchart of a program to be executed by the controller 10 to obtain the accumulated time value $T_d$. The illustrated program must start to execute in response to turning ON the ignition switch 26. Immediately after starting execution, the current real time data $T_{on}$ is obtained from the vehicle clock 34 and latched. The latched real time data $T_{on}$ is written into a register 54 in the input unit 12, at a step 100. The real time data $T_{on}$ will be hereafter referred to as "On time".

The On time $T_{on}$ and real-time data $T_{off}$ which is written into a predetermined address 60 of RAM 18 when the ignition switch was last turned OFF, and which will be referred to hereafter as "OFF time", are read out at a step 110. In the step 110, the period of time $T_r$ for which the ignition switch 20 was turned OFF position, which will be referred hereafter to as "ignition-OFF time", is derived from the difference between the on time and the off time. At a step 120, the ignition-OFF time $T_r$ is subtracted from the accumulated time value T stored in an address 56 in RAM after the ignition switch 20 was last turned OFF, in order to obtain an initial time value $T_d$. The calculation of the initial time value $T_d$ in step 120 is performed according to the following equation:

$$T_d = T - 4 \times T_r$$

When the subtrahend ($4T_r$) is larger than the carry-over time value T, an address 58 in which the accumulated driving time value $T_d$ is stored is cleared to restart accumulation of the travelling or driving time value $T_d$ from zero. Otherwise, the remaining driving time value $T_d$ is written into the address 58 of the RAM.

Figure 5:
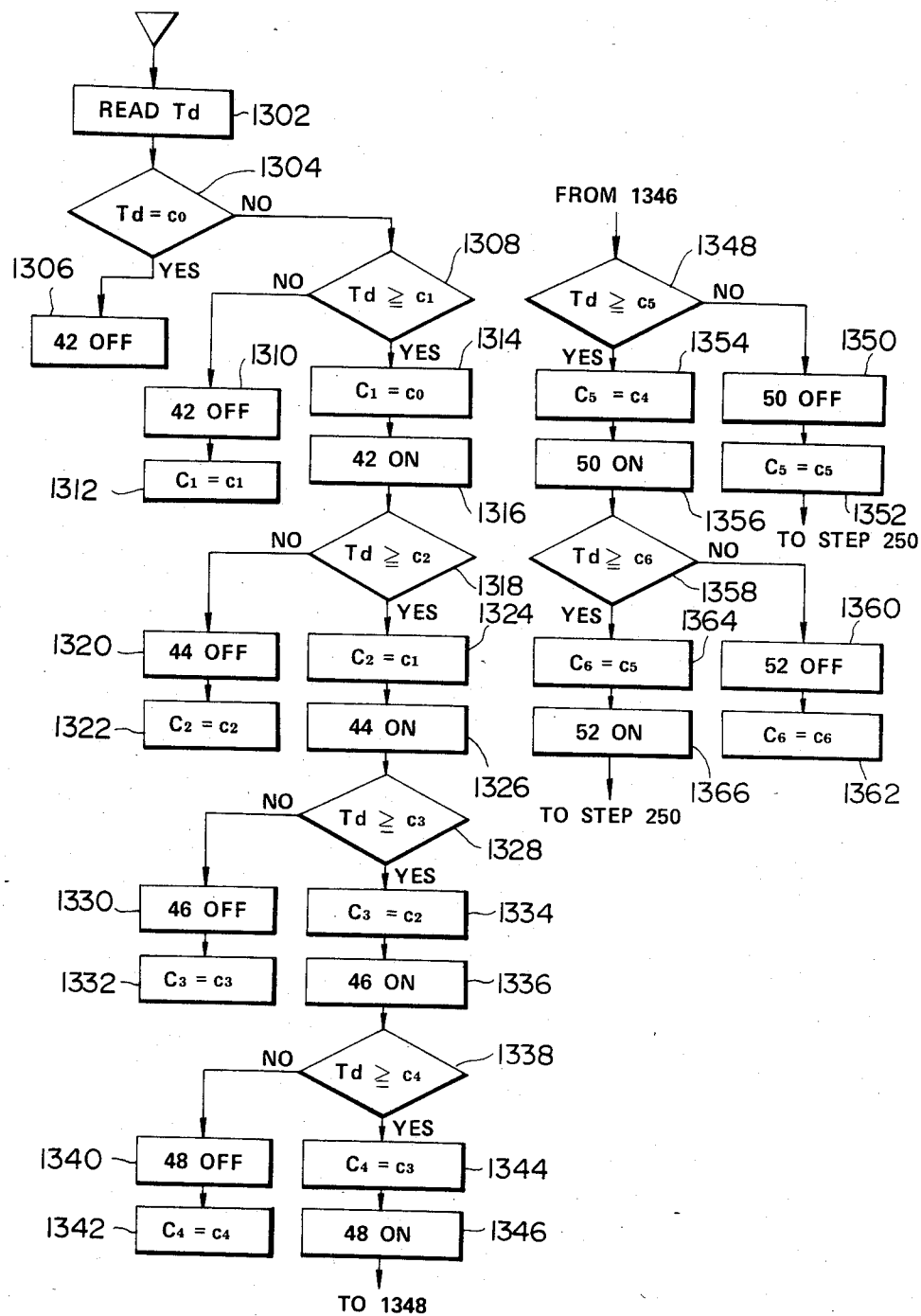
FIG. 5 is a flowchart of a program executed as a sub-routine of the main routine of FIG. 4.

After the step 120, a display control subroutine, which will be described in detail with reference to FIG. 5, is executed at a step 130 in order to visually indicate the level of remaining fatigue soon after the engine starts up.

As a general rule, the driver should take a long enough rest to turn all of the indicator segments 42, 44, 46, 48 and 50 OFF. Although the shown embodiment requires a resting period one-fourth as long as the driving period, the rate of rest in relation to the total elapsed driving time can be adjusted in any way as long as the required rest period is sufficient to allow the driver to completely recover from fatigue.

After execution of the display control subroutine at the step 130, the vehicle condition is checked at a step 140. If the vehicle is running, i.e. if vehicle rest conditions described above are not satisfied at the step 140, the counter-A 20 is enabled and the counter-B 22 is disabled, at a step 150. In the enabled condition, the counter-A counts the clock pulses from the clock pulse generator 36 and outputs a counter signal indicative of the measured driving period $t_A$ which will be referred to hereafter as "driving time counter value". The CPU reads the driving time counter value $t_A$ at a step 160 and clears the counter value in the counter-A 20.

At a step 170, the driving time counter value $t_A$ is added to the driving time data $T_d$ stored in the address 58 of RAM to derive a new driving time value $T_d$. The content of the RAM address 58 is updated with the newly derived accumulated driving time value $T_d$ at a step 230.

On the other hand, if the vehicle is at rest and thus the answer of the step 140 is NO, the counter-A 20 is disabled and its counter value is cleared in step 180. At the same time, the counter-B 22 is then enabled to count clock pulses and to output a counter signal indicative of the counter value $t_B$ which will be referred to hereafter as "resting time counter value". The CPU reads out the resting time counter value $t_B$ at a step 190. Then, the value of a FLAG register 27 in the controller 10 is checked at a step 195. If the FLAG register 27 has been reset and thus the value thereof is zero, the resting time counter value $t_B$ is compared with a resting time threshold $t_{ref}$ at a step 200.

When the resting time counter value $t_B$ is less than the resting time threshold $t_{ref}$ the vehicle driving condition is checked again at a step 202. If the vehicle has remained at rest and thus the answer at the step 202 is NO, process control jumps to a step 250 to be described later. On the other hand, when the vehicle is detected to be moving at the step 202, then the FLAG register 27 is reset to zero at a step 204. After resetting the FLAG register, the resting time counter value $t_B$ is added to the accumulated driving time value $T_d$ stored in the RAM address 58 at a step 210 since the vehicle has only stopped briefly due to some traffic conditions or the like.

When at step 200 the resting time counter value $t_B$ is equal to or greater than the resting time threshold $t_{ref}$ the resting time counter value $t_B$ is multiplied by four and then the product is subtracted from the accumulated driving time data $T_d$ at a step 220. After this, the counter-B 22 is then cleared at a step 222, and 224 to indicate that the vehicle has been stopped long enough for the driver to rest.

After the FLAG register has been set, as long as the vehicle remains at rest, the resting time counter value $t_B$ read out at the step 190 will be multiplied by four and subtracted from the accumulated driving time value $T_d$ by jumping from the step 195 to the step 220 everytime through the loop to be described later. The new accumulated driving time value $T_d$ derived at steps 170, 210 and 220 are used to update the old accumulated driving time value in the RAM address 58 at a step 230. After this, again, the display control sub-routine shown in FIG. 5 is executed at a step 240. At the end of the display control sub-routine, the process returns to the main routine of FIG. 4, specifically to a subsequent step 250.

At step 250, the ignition switch position is checked. When the ignition switch 26 is in the ON position, control returns to the step 140 to begin the next iteration of the loop 140-195-200-230-250. On the other hand, when the ignition switch 26 is turned OFF, the instantaneous real-time data supplied by the vehicle clock 34 is latched and written into the address 60 of RAM 18 at a step 260. The driving time value $T_d$ is then transferred to the address 56 (T) of RAM 18 which should be non-volatile, at a step 270. This final step allows the driving time value $T_d$ to be carried over from driving session to driving session so that the compensatory effects of varying rest periods can be accurately taken into account. Thereafter, program ends.

The display control sub-routine executed in steps 130 and 240 as set forth above is illustrated in the flowchart of FIG. 5.

Immediately after starting execution of the display control sub-routine, the driving time value $T_d$ is accessed from the address 58 of RAM at a step 1302. The driving time value $T_d$ is compared with the zero indicator threshold $c_1$ stored in a memory section $C_0$ in a memory block 62 holding the various threshold values $c_0$ to $c_6$ in individual addresses $C_0$ to $C_1$ at a step 1304. The zero threshold $c_0$ stored in the cell $C_0$ of the block 62 is representative of a null value. Therefore, the answer at step 1304 will be YES only when the accumulated driving time value $T_d$ is zero. If the answer at the step 1304 is YES, the first indicator segment 42 is turned OFF at a step 1306. After the step 1306, execution of the display control sub-routine returns to the main routine (either step 140 or step 250).

On the other hand, if the answer at the step 1304 is NO, i.e. if there is some accumulated driving time, the driving time value $T_d$ is compared with the first indicator threshold $c_1$ stored in the cell $C_1$ of the block 62 of RAM, at a step 1308. When the driving time value $T_d$ is less than the first indicator threshold $c_1$, the first indicator segment 42 is turned OFF at a step 1310. The contents of the cell $C_1$ of the address 62 are then updated with the first indicator threshold $c_1$, at a step 1312. This step 1312 is necessitated by a step 1314 which will be described later. After the step 1312, the execution of the display control sub-routine terminates and returns to the main routine. If the driving time value $T_d$ is equal to or larger than the threshold $c_1$ in step 1308, the contents of the cell $C_1$ are replaced by zero, i.e. the zero indicator threshold $c_0$, at a step 1314. Thereafter, the first indicator segment 42 is turned ON, at a step 1316. The driving time value $T_d$ is further compared with the second indicator threshold $c_2$, at a step 1318. When the driving time data $T_d$ is less than the second indicator threshold $c_2$, the second indicator 44 is turned OFF, at a step 1320.

After this step 1320, the cell $C_2$ is updated with the value corresponding to the second indicator threshold $c_2$. Thereafter, the execution of the display control subroutine terminates and returns to the main routine.

When the driving time value $T_d$ is equal to or greater than the second indicator threshold $c_2$, the cell $C_2$ of the block 62 of RAM is updated with a value corresponding to the first indicator threshold $c_1$, at a step 1324. Then, the second indicator segment 44 is turned ON at a step 1326. Subsequent to the step 1326, the driving time value $T_d$ is compared with the third indicator threshold $c_3$, at a step 1328. When the driving time value $T_d$ is less than the third indicator threshold $c_3$, the third indicator segment 46 is turned OFF at a step 1330 and thereafter, the cell $C_3$ is updated with a value corresponding to the third indicator threshold $c_3$ at a step 1332. Then, the display control sub-routine terminates and returns control to the main routine.

When the driving time value $T_d$ is equal to or larger than the third indicator threshold $c_3$ at step 1328, the cell $C_3$ is updated with a value corresponding to the second indicator threshold $c_2$, at a step 1334. Thereafter, the third indicator 46 is turned ON at a step 1336. The driving time value $T_d$ is further compared with the fourth indicator threshold $c_4$ stored in the cell $C_4$ of the block 62 of RAM 18. When the driving time value $T_d$ is less than the fourth indicator threshold $c_4$, the fourth indicator 48 is turned OFF at a step 1340 and the cell $C_4$ is updated with a value corresponding to the fourth indicator threshold $c_4$, at a step 1342. On the other hand, when the driving time value $T_d$ is equal to or larger than the fourth indicator threshold $c_4$, the cell $C_4$ is updated with a value corresponding to the third indicator threshold $c_3$, at a step 1344. Then, the fourth indicator segment 48 is turned ON, at a step 1346. After turning ON the fourth indicator 48, the driving time value $T_d$ is further compared with the fifth indicator threshold $c_5$, at a step 1348. When the driving time value $T_d$ is less than the fifth indicator threshold $c_5$, the fifth indicator segment 50 is turned OFF at a step 1350. Thereafter, the cell $C_5$ storing the fifth indicator threshold $c_5$ is updated with a value corresponding to the fifth indicator threshold $c_5$. Thereafter, control returns to the main routine.

When the driving time data $T_d$ is equal to or larger than the fifth threshold $c_5$ at step 1348, then the cell $C_5$ is updated with a value corresponding to the fourth indicator threshold $c_4$ at a step 1356. Subsequent to the step 1356, the fifth indicator segment 50 is turned ON at a step 1358 and the driving time value $T_d$ is further compared with an alarm threshold $c_6$ stored in a cell $C_6$ of the block 62 of RAM 18. When the driving time data $T_d$ is less than the alarm threshold $c_6$, the alarm indicator 52 is turned OFF, at a step 1360. After this, the cell $C_6$ of the block 62 is updated with a value corresponding to the alarm threshold $c_6$, at a step 1362. If the driving time value $T_d$ is equal to or more than the alarm threshold $c_6$, the cell $C_6$ of the block 62 is updated with a value corresponding to the fifth indicator threshold $c_5$ at a step 1364 and the alarm indicator 52 is turned ON at a step 1366.

After processing of the steps 1362 and 1366, control passes to one of steps 140 or 250 of the main routine.

The relationship between changes in the activation states of the indicator segments and the threshold values can be summarized by the following table:

| Indicator | OFF → ON | ON → OFF |
| --- | --- | --- |
| 42 | $T_d \geq c_1$ | $T_d = c_0 (C_1)$ |
| 44 | $T_d \geq c_2$ | $T_d < c_1 (C_2)$ |
| 46 | $T_d \geq c_3$ | $T_d < c_2 (C_3)$ |
| 48 | $T_d \geq c_4$ | $T_d < c_3 (C_4)$ |
| 50 | $T_d \geq c_5$ | $T_d < c_4 (C_5)$ |
| 52 | $T_d \geq c_6$ | $T_d < c_5 (C_6)$ |

As will be appreciated from the foregoing description and the table, once the indicator segment has been turned ON, it will not be turned OFF until the driving time value $T_d$ drops to the one level lower than the turning ON level. For instance, in order to turn the first indicator segment 42 ON, the driving time value $T_d$ must be equal to or greater than the first indicator threshold $c_1$. However, the first indicator segment 42 will thereafter remain ON until the driving time value drops to zero, i.e. until it matches the zero indicator threshold $c_0$.

By means of the procedure of FIG. 5, hunting of the activation states of the individual indicator segments can be satisfactorily prevented.

While the specific embodiment has been disclosed in detail to fully describe the invention, it should be appreciated that it is possible to embody the present invention in other ways while still performing the same or similar alarm operations. Therefore, the invention should be understood or interpreted to include all such possible embodiments and modifications of the shown embodiment which do not depart from the principle of the appended claims.

What is claimed is:

1. A fatigue alarm system for an automotive vehicle driver comprising:
    a first means for measuring the period of time for which an ignition switch of the vehicle remains ON and outputting a first signal having a value representative of the measured driving time;
    a second means for measuring the period of time for which said ignition switch remains OFF and outputting a second signal having a value representative of the measured resting time;
    a detector for detecting when the vehicle is at rest while said ignition switch is ON and producing a detector signal at such times;
    a third means, responsive to said detector signal, for measuring the period of time for which said detector signal continues and outputting a third signal having a value representative of the measured stopping time;
    a fourth means for subtracting said second signal value from said first signal value to derive an accumulated driving time value, said fourth means comparing said third signal value with a first threshold and, when said third signal value is less than said first threshold, adding said third signal value to said accumulated driving time value, and when said third signal value is greater than said first threshold, subtracting said third signal value from said accumulated driving time value, and the fourth means further comparing said accumulated driving time value with a second threshold and producing an alarm signal when said accumulated driving time value is greater than said second threshold; and
    an alarm means, responsive to said alarm signal from said fourth means for producing an alarm.

2. The system as set forth in claim 1, wherein said second means is associated with a vehicle clock measuring real time to record the instantaneous real time at the moments at which said ignition switch is turned ON and OFF.

3. The system as set forth in claim 1, wherein said detector comprises a parking brake switch detecting application of a parking brake.

4. The system as set forth in claim 1, wherein said detector comprises an automatic transmission park position switch detecting when an automatic transmission is in its parking gear.

5. The system as set forth in claim 3, wherein said detector further comprises an automatic transmission park position switch detecting when an automatic transmission is in its parking gear.

6. The system as set forth in claim 1, wherein said alarm means comprises a visual display including a plurality of indicator segments and an alarm segment turned ON in response to said alarm signal, said indicator segments being adapted to indicate the level of accumulated driver fatigue, each of said indicator segments being activated when said accumulated driving time value exceeds a corresponding given value which corresponds to a level of fatigue.

7. The system as set forth in claim 6, which further comprises a fifth means associated with said indicator segments to decrease each of said given values by a given amount while the corresponding one of said indicator segments is activated.

8. The system as set forth in claim 7, wherein said fifth means is further associated with said fourth means to lower said second threshold by a given amount when said alarm segment is ON.

9. A fatigue alarm method for an automotive vehicle driver comprising the steps of:
    measuring the periods of time for which an automotive vehicle is moving and at rest;
    comparing the measured rest periods of the vehicle with a first predetermined threshold value;
    adding the rest periods to the moving periods when the rest periods do not exceed said first threshold value to obtain an accumulated driving time value;
    subtracting the rest periods from said accumulated driving time value when the rest periods exceed said first threshold value to update said driving time value; and
    notifying the driver of the vehicle of excessive fatigue when the updated driving time value exceeds a second predetermined threshold value.

10. The method of claim 9, further comprising the step of multiplying the rest periods to be subtracted from the driving time value by a factor representative of the ratio between the driving time and the resting time required to produce and correct, respectively, equal levels of driver fatigue.

11. The method of claim 10, further comprising the step of continuously indicating to the driver the current updated driving time value in order to provide some indication of the current level of driver fatigue.

12. The system as set forth in claim 6 further comprising fifth means for turning ON respective ones of said indicator segments when said accumulated driving time value exceeds corresponding respective first threshold values and for turning OFF said respective indicator segments when said accumulated driving time value decreases below corresponding respective second threshold values lower than said respective first threshold values.

13. The system as set forth in claim 12 wherein said fifth means is operable for turning ON one of said indicator segments at one threshold value of said accumulated driving time and for turning ON a second of said indicator segments at another threshold value of said accumulated driving time higher than said one threshold value and for turning OFF said second indicator segment when said accumulated driving time value decreases below said one threshold value.

14. A fatigue alarm system for an automotive vehicle driver comprising:
- a first means for measuring the period of time for which an ignition switch of the vehicle remains ON and outputting a first signal having a value representative of the measured driving time;
- a second means for measuring the period of time for which said ignition switch remains OFF and outputting a second signal having a value representative of the measured resting time;
- a detector for detecting when the vehicle is at rest while said ignition switch is ON and producing a detector signal at such times;
- a third means, responsive to said detector signal, for measuring the period of time for which said detector signal continues and outputting a third signal having a value representative of the measured stopping time;
- a fourth means for subtracting said second signal value from said first signal value to derive an accumulated driving time value;
- rest detecting means for differentiating between stops during ignition switch ON time periods providing rest for the vehicle driver and stops during ignition switch ON time periods which do not provide rest for the vehicle driver,
- said rest detecting means including threshold means for determining whether a stop during an ignition switch ON time period exceeds a threshold value and, when said stop during an ignition switch ON time period is less than said threshold value, causing said fourth means to add said third signal value to said accumulated driving time value thereby adding said stop during the ignition switch ON time period to said accumulated driving time value while, when said stop during an ignition switch ON time period is greater than said threshold value, causing said fourth means to subtract said third signal value from said accumulated driving time value thereby subtracting said stop during an ignition switch ON time period from said accumulated driving time value;
- said fourth means being further operable for comparing said accumulated driving time value with a further threshold value and for producing an alarm signal when said accumulated driving time value is greater than said second threshold value; and
- an alarm means, responsive to said alarm signal from said fourth means, for producing an alarm.

* * * * *